US00PP21075P2

(12) United States Plant Patent
Maranto

(10) Patent No.: US PP21,075 P2
(45) Date of Patent: Jun. 22, 2010

(54) GRAPEVINE PLANT NAMED 'ROMA SEEDLESS'

(50) Latin Name: *Vitis vinifera*
Varietal Denomination: Roma Seedless

(75) Inventor: Joseph Maranto, Bakersfield, CA (US)

(73) Assignee: Anton Caratan & Son, Delano, CA (US)

( * ) Notice: Subject to any disclaimer, the term of this patent is extended or adjusted under 35 U.S.C. 154(b) by 10 days.

(21) Appl. No.: 12/320,460

(22) Filed: Jan. 27, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent L Bell
(74) *Attorney, Agent, or Firm*—Buchanan Ingersoll & Rooney PC

(57) ABSTRACT

A new and distinct variety of grapevine is provided which abundantly forms attractive medium-to-large seedless berries having a rose-pink skin coloration in medium-to-large substantially uniform clusters. The fruit displays a sweet crisp flavor and is firm in texture. The fruit commonly is ready for harvest during late October or early November in the San Joaquin Valley of Central California, U.S.A., and displays significant crispness and good eating qualities as a table grape. The fruit firmness renders the fruit well amenable for handling, shipping, and storage. The fruit commonly is more elongated and less round and lighter in coloration than that of the 'Mara Seedless' variety (U.S. Plant Pat. No. 19,599).

1 Drawing Sheet

Botanical/commercial classification: *Vitis vinifera*/Grapevine.

Varietal denomination: cv. Roma Seedless.

BACKGROUND OF THE NEW VARIETY

New grapevine varieties are being sought which display a combination of outstanding characteristics in areas such as vigor, seedlessness, productivity, and resistance to diseases and pests. Characteristics such as fruit size, coloration, flavor and taste also are of prime importance when evaluating new varieties of grape plants.

The new variety of *Vitis vinifera* was created by artificial pollination during the course of a grapevine breeding program wherein two parents were crossed which previously had been studied in the hope that they would contribute the desired characteristics. Such breeding program was initiated during 1992 near Delano in the San Joaquin Valley of Central California, U.S.A. The cross that resulted in the creation of the new variety of the present invention was made in 1993. Both parents of the new variety were grape varieties being grown commercially in the United States. The female parent (i.e. the seed parent) of the new variety was the 'Red Globe' seeded grape variety (U.S. Plant Pat. No. 4,787). The male parent (i.e. the pollen parent) of the new variety was the 'Crimson' seedless grape variety (non-patented in the United States). The 'Crimson' male parent was released by the U.S.D.A. at Fresno, Calif., U.S.A., during 1989, and was formed by the cross of the 'Emperor' variety (non-patented in the United States) and an unreleased seedling named 'C33-1-99' (non-patented in the United States).

The parentage of the new variety can be summarized as follows:

'Red Globe'×'Crimson'.

The seeds resulting from the above pollination were sown and 125 small seedling plants were obtained which were physically and biologically different from each other. The resulting seedling plants were evaluated in detail and the new variety of the present invention was selected and was initially designated as 22-93, with the mother plant being Vine No. 173 of Row No. 80.

It was found that the new grapevine of the present invention possesses the following combination of characteristics:

(a) forms attractive medium-to-large seedless berries having a rose-pink skin coloration in medium-to-large substantially uniform clusters which display a sweet crisp flavor, (b) commonly bears fruit during late October or early November in the San Joaquin Valley of Central California, U.S.A., and (c) bears fruit that is crisp and firm and is well amenable for storage, handling, and shipping.

The fruit of the new variety is considered to be seedless. However, occasionally a few very small traces of seeds have been observed.

The new variety during observations to date has displayed no visible disease, and has displayed an ability to well resist cold, drought, heat and wind. The fruit of the new variety has been found to display excellent handling and shipping qualities combined with desirable dessert eating qualities.

The new variety of the present invention can be readily distinguished from its ancestors. More specifically, the 'Red Globe' parent forms large clusters of berries having a different shape which possess seeds and which mature approximately one month earlier than the new variety, and the 'Crimson' variety forms smaller berries which display lesser rose pink coloration in a less uniform in its presentation.

The typical ripening date of the new variety is later than that of the 'Mara Seedless' variety (U.S. Plant Pat. No. 19,599). Also, the fruit of the 'Mara Seedless' variety commonly is darker in coloration, possesses a softer internal flesh, and is more round and less elongated.

The new variety of the present invention has been found to undergo asexual propagation beginning in 1998 near Delano in the San Joaquin Valley of Central California, U.S.A. by grafting on mature 'Thompson Seedless' rootstock (non-patented in the United States). Such asexual propagation has been conducted thereafter in successive years through 2006, and has shown that the characteristics of the new variety are strictly transmissible from one generation to another. Accordingly, the new variety undergoes asexual propagation in a true-to-type manner.

The new variety has been named 'Roma Seedless'.

BRIEF DESCRIPTION OF THE PHOTOGRAPH

The accompanying photograph shows as nearly true as it is reasonably possible to make in a color illustration of this character typical specimens of the new variety. The photograph includes typical substantially uniform clusters of the attractive rose-pink grapes, upper (right) and under (left) surfaces of the leaves, and berries that are transversely (right) and longitudinally (left) sectioned in order to reveal the flesh which lacks seeds.

Dimensions in centimeters are included at the top of the photograph for comparative purposes.

DETAILED DESCRIPTION

The chart used in the identification of colors is the Dictionary of Color by A. Maerz and M. Rea Paul (1930). Common color terms are to be accorded their ordinary dictionary significance. The description is based on the observation of plants of the new variety while growing on 'Thompson Seedless' rootstock outdoors near Delano in the San Joaquin Valley of Central California, U.S.A.

Vine:

*Vigor.*—Exceeds that of its 'Red Globe' and 'Crimson' parental varieties.

*Productive capacity.*—Very productive with spur pruning.

*Trunk.*—Slender, includes long split strips, and ten years after grafting the diameter commonly is approximately 3.5 inches (approximately 89 mm) measured 1 foot above the graft union.

*Bark color.*—Brown (8-T-11) Montella, and light brown (7-E-7) underbark.

*Cane length.*—Medium, and commonly approximately 5 to 7 feet (approximately 1.5 to 2.1 m).

*Cane width.*—Medium, and commonly approximately 0.5 inch (approximately 13 mm) at node.

*Nodes.*—Generally round in configuration, and commonly spaced at a distance of 3 to 4 inches (approximately 76 to 102 mm).

*Shoot configuration.*—Substantially circular to slightly flattened, approximately 10 mm in diameter, and with longitudinal striations.

*Shoot color.*—Light green (28-B-2).

*Shoot texture.*—Smooth.

*Growing tip.*—Generally ascends straight up.

*Tendril length.*—Commonly approximately 4 to 6 inches (approximately 102 to 152 mm), and substantially conical in configuration.

*Tendril location.*—Few, and discontinuous.

*Tendril form.*—Bifurcated and trifurcated.

*Tendril texture.*—Smooth.

*Tendril color.*—(21-C-5).

*Bud shape.*—Pointed conical.

*Bud length.*—Commonly approximately 6 mm.

*Bud width.*—Commonly approximately 5 mm.

*Bud break.*—Commonly at the middle to the end of March at the specified location, with most of the basal buds being fruitful.

Leaves:

*Size.*—Generally medium.

*Density.*—Heavy.

*Length.*—Approximately 4.0 inches (approximately 102 mm) on average for a mature leaf.

*Width.*—Approximately 4.2 inches (approximately 106 mm) on average for a mature leaf.

*Color.*—Dark green (24-J-7) on the dorsal surface, and light green (23-H-6) on the ventral surface.

*Texture.*—Smooth and glabrous on both surfaces.

*Petiole length.*—Commonly approximately 3.2 inches (approximately 82 mm).

*Petiole diameter.*—Commonly approximately 4 mm.

*Petiole sinus.*—U-shaped.

*Petiole color.*—Light green (23-J-1).

*Lobe.*—Five-pointed.

*Color midrib.*—Grape green (21-K-7).

*Margins.*—Serrate with irregular teeth, commonly approximately 12 teeth per lobe, and approximately 50 to 60 teeth on entire leaf.

Flowers:

*Date of bloom.*—Approximately middle of May at the specified location.

*Date of full bloom.*—Commonly third week of May at the specified location.

*Size.*—Commonly approximately 0.4 cm at full bloom.

*Type.*—Fertile.

*Location.*—Primarily at the second or third node from the base with fruitfulness upon spur pruning.

*Petals.*—Five in number, and open from the bottom to the top.

*Petal color.*—Light green (23-J-6).

*Sepals.*—Five in number, and commonly poorly developed.

*Stamen.*—Six in number, and upright and diverging.

*Pollen.*—Abundant, and yellow (9-L-4) Sunflower Dandelion in coloration.

*Pistil.*—One in number, and produces a liquid to hold pollen to achieve germination.

*Filaments.*—Approximately 4 mm in length, and green (22-L-4) Calla green in coloration.

Fruit:

*Time.*—Commonly ripe for commercial harvesting and shipment during late October or early November at the specified location.

*Berry size.*—Medium to large.

*Berry form.*—Substantially uniform.

*Berry shape.*—Ellipsoidal elongated, and commonly more elongated than the 'Mara Seedless' variety.

*Berry length.*—Commonly approximately 1.1 inches (approximately 27 mm) along the longitudinal axis.

*Berry width.*—Commonly approximately 0.8 inch (approximately 20 mm).

*Berry number.*—Commonly approximately 120 to 150 per cluster on average.

*Berry weight.*—Commonly approximately 6 to 7 grams on average. When sprayed with the plant hormone gibberellic acid the berry weight commonly increases.

*Cluster form.*—Substantially uniform and commonly conical shouldered, and compact.

*Cluster size.*—Medium to large.

*Cluster length.*—Commonly approximately 7 to 9 inches (approximately 17.8 to 23 mm) on average.

*Cluster weight.*—Commonly approximately 600 to 1000 grams on average.

*Peduncle length.*—Commonly approximately 1.3 inches (approximately 33 mm).

*Solids.*—Approximately 20 percent sugar on Nov. 3, 2008.

*Acidity.*—Approximately 0.43 percent tritrable acidity.

*Sugar/acid ratio.*—Approximately 46.5.

*Juice pH.*—Approximately 3.7.

*Seeds.*—Seedless, with an occasional few very small traces of seeds.

*Capstem.*—Strong with long chalazas attached to vascular tissue.

*Pedicel.*—Approximately 0.3 inch (approximately 7 mm) in length.

*Skin thickness.*—Relatively thin.

*Skin texture.*—Very firm.

*Skin cracking.*—No tendency to crack under observations to date.

*Skin color.*—Red pink (7-J-8) Domingo, and commonly lighter in coloration than that of the 'Mara Seedless' variety. Seasonal temperature variation during ripening has been observed to sometimes influence the development of color.

*Lenticels.*—None visible.

*Flesh color.*—Light pinkish (7-E-8).

*Flavor.*—Sweet and crisp.

*Eating quality.*—Crisp, good and meaty. This can be compared to the softer internal texture of the fruit of the 'Mara Seedless; variety.

*Use.*—Dessert, table grape.

*Keeping quality.*—Very good, after one month in storage, still displays a good appearance.

Development:

*Resistance to diseases.*—No disease problem has been encountered during observations to date.

*Resistance to cold.*—Good.

*Resistance to drought.*—Good.

*Resistance to heat.*—Good.

*Resistance to wind.*—Good.

*Shipping and handling.*—excellent.

When the new variety is grown near Delano, Calif., U.S.A., no winter damage has been encountered during observations to date. Over the past twenty years low temperatures at such location have ranged from approximately 29° F. to 13° F. Tule fog commonly is present at this growing area during the winter. The winter cold that is encountered at such location is adequate to satisfy the vine dormancy requirement.

The growing area near Delano, Calif., U.S.A. is present in U.S.D.A. Hardiness Zone No. 5 to 6. This area is famous for the production of table grapes with high temperatures during the summer of approximately 105° F. to 108° F. sometimes being encountered. Rain is sparse to non-existent during the summer and almost constant sunshine is experienced during the growing season.

The 'Roma Seedless' variety has not been observed under all possible environmental conditions to date. Accordingly, it is possible that the phenotypic expression may vary somewhat with changes in light intensity and duration, cultural practices, and other environmental conditions.

I claim:

1. A new distinct grapevine plant characterized by the following combination of characteristics:

(a) forms attractive medium-to-large seedless berries having a rose-pink skin coloration in medium-to-large substantially uniform clusters which display a sweet crisp flavor, (b) commonly bears fruit during late October or early November in the San Joaquin Valley of Central California, U.S.A., and (c) bears fruit that is crisp and firm and is well amenable for storage, handling, and shipping;

substantially as herein shown and described.

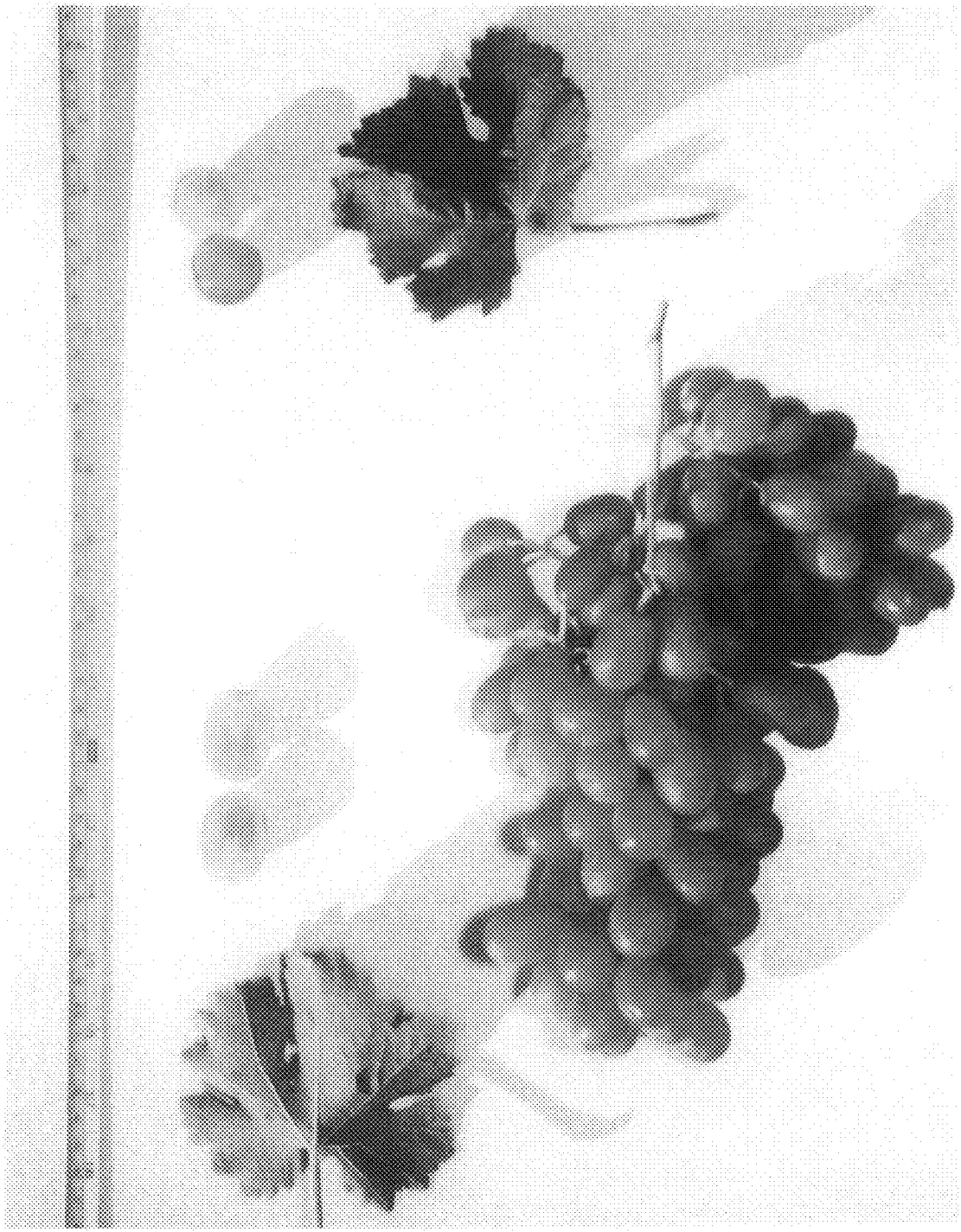

* * * * *